United States Patent
Luijten et al.

(10) Patent No.: US 12,259,503 B2
(45) Date of Patent: Mar. 25, 2025

(54) METHOD AND SYSTEM FOR ADAPTIVE BEAMFORMING OF ULTRASOUND SIGNALS

(71) Applicant: KONINKLIJKE PHILIPS N.V., Eindhoven (NL)

(72) Inventors: Wouter Marinus Benjamin Luijten, Eindhoven (NL); Ruud Johannes Gerardus Van Sloun, Eindhoven (NL); Frederik Jan De Bruijn, Eindhoven (NL); Harold Agnes Wilhelmus Schmeitz, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 710 days.

(21) Appl. No.: 17/288,043

(22) PCT Filed: Oct. 22, 2019

(86) PCT No.: PCT/EP2019/078739
§ 371 (c)(1),
(2) Date: Apr. 23, 2021

(87) PCT Pub. No.: WO2020/083918
PCT Pub. Date: Apr. 30, 2020

(65) Prior Publication Data
US 2021/0382157 A1  Dec. 9, 2021

(30) Foreign Application Priority Data

Oct. 25, 2018 (EP) ..................................... 18202469
Mar. 21, 2019 (EP) ..................................... 19164249

(51) Int. Cl.
*G01S 7/52* (2006.01)
*G01S 15/89* (2006.01)
(Continued)

(52) U.S. Cl.
CPC ............. *G01S 7/52085* (2013.01); *G06N 3/08* (2013.01); *G10K 11/34* (2013.01); *G01S 15/8915* (2013.01)

(58) Field of Classification Search
CPC ............. G01S 7/52085; G01S 15/8915; G01S 7/52047; G06N 3/08; G10K 11/34
See application file for complete search history.

(56) References Cited

U.S. PATENT DOCUMENTS

| | | | |
|---|---|---|---|
| 2014/0135625 A1* | 5/2014 | Konofagou | A61B 8/467 600/443 |
| 2015/0119701 A1* | 4/2015 | Vignon | A61B 8/14 600/424 |
| 2021/0132223 A1* | 5/2021 | Hennersperger | G06N 3/08 |

FOREIGN PATENT DOCUMENTS

| | | | |
|---|---|---|---|
| CN | 106456115 A | * 2/2017 | ........... A61B 8/4483 |
| EP | 0575716 A1 | 12/1993 | |
| WO | 2018127498 A1 | 7/2018 | |

OTHER PUBLICATIONS

Luchies et al. ("Deep Neural Networks for Ultrasound Beamforming", IEEE Transactions On Medical Imaging, vol. 37, No. 9, Feb. 27, 2018 (Feb. 27, 2018), pp. 2010-2021) (Year: 2018).*

(Continued)

*Primary Examiner* — Luke D Ratcliffe
*Assistant Examiner* — Christopher Richard Walker (57) ABSTRACT

The invention relates to a method for adaptive beamforming of ultrasound signals, the method comprising the steps of (a) Receiving time-aligned RF signals acquired by multiple ultrasound transducer elements in response to an ultrasound transmission; (b) Determining content-adaptive apodization weights for beamforming the time-aligned RF signals by applying a trained artificial neural network (16) to the time-aligned RF signals; and (c) Applying the content-adaptive apodization weights to the time-aligned RF signals (Continued)

to calculate a beamformed output signal. The invention also relates to a method for training an artificial neural network (16) useful in adaptive beamforming of ultrasound signals, and a related computer program and system.

20 Claims, 8 Drawing Sheets

(51) Int. Cl.
*G06N 3/08* (2023.01)
*G10K 11/34* (2006.01)

(56) References Cited

OTHER PUBLICATIONS

Preiswerk et al. ("Synthesizing dynamic MRI using long-term recurrent convolutional networks." Machine Learning in Medical Imaging: 9th International Workshop, MLMI 2018, Held in Conjunction with MICCAI 2018, Granada, Spain, Sep. 16, 2018) (Year: 2018).*
CN106456115 (attached machine translation) (Year: 2017).*
Byram et al. ("Physics and data driven models for ultrasound image reconstruction," 2017 51st Asilomar Conference on Signals, Systems, and Computers, Pacific Grove, CA, USA, 2017, pp. 1012-1015) (Year: 2017).*
Wikipedia contributors. (2018). Activation function. Wikipedia. https://en.wikipedia.org/w/index.php?title=Activation_function &oldid=862806937 (Year: 2018).*
Shang et al., ("Understanding and Improving Convolutional Neural Networks via Concatenated Rectifier Linear Unit", Proceedings of the 33rd International Conference on Machine Learning, New York, USA, 2016.) (Year: 2016).*
International Search Report and Written Opinion of PCT/EP2019/078739, dated Jan. 20, 2020.
Thomenius, K.E. "Evolution of Ultrasound Beamformers" 1996 IEEE Ultrasonic Symp. Proc. vol. 2, pp. 1615-1622.
Holfort, I.K. "Adpative Beamforming for Medical Ultrasound Imaging", PhD Thesis, Technical University of Denmark, Nov. 2009.
Synnevag, J.F. et al "Benefits of Minimum-Variance Beamforming in Medical Ultrasound Imaging", IEEE Transactios Ultrason. Ferroelect. Frequ. Control, vol. 56, No. 9, pp. 1868-1879, 2009.
Luchics, Adam et al "Suppressing Off-Axis Scattering using Deep Neural Networks" Proceedings of SPIE 10580, Medical Imaging 2018, Ultrasonic Imaging and Tomography 105800G, Mar. 2018.
Shang, et al "Understanding and Improving Convolutional Neural Networks via Concatenated Rectifier Linear Unit", Proceedings of the 33rd International Conf. On Machine Learning, 2016.
Chollet, F. "Antirectifier," GitHub, 2018. [Online]. Available: https://github.com/kerasteam/keras/blob/4f2e65c385d60fa87bb143c6c506cbe428895f44/examples/antirectifier.py.
Anas, Emran Mohammad Abu et al "Robust Photoacoustic Beamforming Using Dense Convolutional Neural Networks", LNCS 11042, pp. 3-11, 2018.
Luchies, Adam C et al "Deep Neural Networks for Ultrasound Beamforming", IEEE Transactions On Medicla Imaging, vol. 37, No. 9, Sep. 2018.
Senouf, Ortal et al "High Frame-Rate Cardiac Ultrasound Imaging with Deep Learning", Aug. 2018.
Montaldo, Gabriel et al "Coherent Plane-Wave Compounding for Very High Frame Rate Ultrasonography and Transient Elastography", IEEE Transactions On Ultrasonics, Ferroelectrics, and Frequency Control, vol. 56, No. 3, Mar. 2009.

* cited by examiner

METHOD AND SYSTEM FOR ADAPTIVE BEAMFORMING OF ULTRASOUND SIGNALS

CROSS-REFERENCE TO PRIOR APPLICATIONS

This application is the U.S. National Phase application under 35 U.S.C. § 371 of International Application No. PCT/EP2019/078739, filed on Oct. 22, 2019, which claims the benefit of European Patent Application No. 18202469.5, filed on Oct. 25, 2018 and European Patent Application No. 19164249.5, filed on Mar. 21, 2019. These applications are hereby incorporated by reference herein.

FIELD OF THE INVENTION

The invention relates to a method for adaptive beamforming of ultrasound signals, a method for training an artificial neural network useful in adaptive beamforming of ultrasound signals, and a related computer program and system.

BACKGROUND OF THE INVENTION

Traditional ultrasound imaging methods usually use delay-and-sum (DAS) beamforming because of its low complexity and fast reconstruction time, as described in K. E. Thomenius, "Evolution of ultrasound beamformers," 1996 *IEEE Ultrason. Symp. Proc.*, vol. 2, pp. 1615-1622, 1996. This method uses fixed, content invariant, apodization weights for the receiving channels. While its reconstruction speed allows real-time imaging, DAS beamforming does not provide optimal image contrast and resolution, because of its lack of content-adaptive array apodization. For example, backscatter from off-axis components is not adequately compensated for. To improve this relatively poor quality, an improved image is often obtained by compounding multiple acquisitions and/or using focused beams, both at the expense of increased acquisition time.

Adaptive beamforming algorithms improve on this by determining optimal content-adaptive apodization weights based on the acquired RF signals and applying them to the receiving channels. However, these methods are computationally more demanding and therefore result in a significantly longer reconstruction time. Therefore, the currently known adaptive beamforming algorithms are not suitable for real-time ultrasound imaging.

A known adaptive beamforming algorithm is the minimum variance (MV) beamformer, in which the apodization weights are continuously optimized to minimize the variance of the received signals after apodization, while maintaining unity gain in the desired direction. This process effectively suppresses the power of interfering signals from undesired directions that typically lead to cluttered images. Although MV beamforming has shown to significantly improve resolution and contrast compared to DAS, it is also notoriously slow, relying on the computationally demanding inversion of an n×n spatial covariance matrix, having a complexity of $n^3$, where n is the number of channels. Therefore, MV beamforming is not used in real-time imaging.

MV beamforming methods are described for example in I. K. Holfort, *Adaptive Beamforming for Medical Ultrasound Imaging*, PhD Thesis, Technical University of Denmark, Lyngby, November, 2009, and J. F. Synnevåg, A. Austeng, and S. Holm, "Benefits of minimum-variance beamforming in medical ultrasound imaging," *IEEE Trans. Ultrason. Ferroelectr. Freq. Control*, vol. 56, no. 9, pp. 1868-1879, 2009. In the context of beamforming, "apodization" may be described as introducing a weighting function (the "apodization weights") across an array, or to the signals acquired by an array. The general principles of beamforming are described e.g. in Chapter Two of the PhD Thesis by I. K. Holfort, *Adaptive Beamforming for Medical Ultrasound Imaging*, and which is incorporated herein by reference.

In MV beamforming, the apodization weights w are determined by solving $$\min w^H R w,$$

subject to $w^H a = 1$, where a is a steering vector and R the covariance matrix of the input array. The solution of this is minimization problem is $$w_{mv} = \frac{R^{-1} a}{a^H R^{-1} a}.$$

Because the inversion of the covariance matrix R is computationally very expensive, especially for large matrices, it is not suitable for real time implementation.

Artificial neural networks have been proposed in the context of ultrasound imaging for image formation and characterization, see for example WO 2018/127498 A1. According to this document, an ultrasound imaging system may include an ultrasound transducer configured to acquire echo signals, as well as a channel memory configured to store the acquired echo signals. The system also includes a neural network coupled to the channel memory and configured to receive one or more samples of the acquired echo signals or of beamformed signals, or both, and to provide imaging data based on the one or more samples of the acquired echo signals. The neural network is trained to produce imaging data or extract tissue information.

According to Adam Luchies and Brett Byram, "Suppressing off-axis scattering using deep neural networks", *Proceedings of SPIE* 10580, *Medical Imaging* 2018: *Ultrasonic Imaging and Tomography*, 105800G, Mar. 6, 2018, the RF signals (also termed channel data) acquired from the ultrasound transducer elements are short-time Fourier transformed and used as input to a deep neural network, which accordingly operates in the frequency domain. The output has the same structure as the input and an inverse short-time Fourier transform is used to convert the processed data back to the time domain, to generate processed channel data, which is summed across channels.

OBJECT OF THE INVENTION

It is an object of this invention to provide an adaptive beamforming method which is capable of providing high image quality, while at the same time having reduced computational cost compared to known content-adaptive beamforming methods. In particular, it is an object of the invention to provide a solution that is capable of providing the same high image quality as traditional adaptive beamforming algorithms, such as MV beamforming, while reducing the computational time to such an extent that it can be used for real-time ultrasound imaging.

SUMMARY OF THE INVENTION

These objects are met or exceeded by a method for adaptive beamforming of ultrasound signals according to claim 1, a method of providing a trained artificial neural network according to claim 13, a computer program according to claim 14 and a system according to claim 15. Any features, advantages or alternative embodiments described herein in relation to the claimed method are also applicable to the other claim categories, in particular the claimed system, computer program and ultrasound imaging device. In particular, the trained neural network can be adapted by the claimed training method. Furthermore, the input data to the artificial neural network can comprise advantageous features and embodiments of the input training data, and vice versa. Furthermore, the output of the trained neural network (the content-adaptive apodization weights) can comprise advantageous features and embodiments of the output training data, and vice versa.

According to a first aspect, the invention provides a method for adaptive beamforming of ultrasound signals, the method comprising the steps of (a) Receiving RF signals acquired by multiple ultrasound transducer elements in response to an ultrasound transmission; and (b) Determining content-adaptive apodization weights for beamforming the RF signals by applying a trained artificial neural network to the RF signals.

Accordingly, the inventive method is able to obtain optimal, or close to optimal, apodization weights, in a content-adaptive fashion, by applying an artificial neural network (NN) as an alternative to the current computationally expensive methods, such as MV beamforming. "Content-adaptive" in this context means that the apodization weights depend on the acquired RF signals, i.e. they are adapted to the content of the signals. In the case of ultrasound imaging, they are adapted to the imaged field-of-view. In contrast to prior art techniques, the output of the NN is not in the form of RF signals (channel data) or a beamformed image, but the output are the apodization weights for each channel, which can then be applied to the RF signals to produce a beamformed output signal in the usual way, e.g. by multiplication and summing. Thus, the input to the NN is the RF signals, and these same signals may then be multiplied with the output of the NN, namely the apodization weights, and subsequently summed, to yield a beamformed output signal.

A complete content-adaptive beamforming or image reconstruction process may be divided into 3 steps: 1) time-of-flight correction, 2) adaptation (and application) of the apodization weights and 3) envelope detection. The inventive method focuses on the calculation of the adaptive apodization weights, which is computationally the most expensive of the above-mentioned 3 steps.

The input to the NN are the radiofrequency (RF) signals acquired by multiple ultrasound transducer elements in response to an ultrasound transmission into a medium, such as a part of the human or animal body. The RF signals as acquired have both amplitude and phase. Thus, RF signals used as input into the NN may be in real or in complex representation. In ultrasound imaging, the area imaged by the ultrasound transmission is termed field-of-view. The multiple ultrasound transducer elements may be a plurality or all elements of an array transducer, for example a linear transducer, or a phased array. In some embodiments, apodization weights will be calculated for all RF signals acquired from the transducer elements in an array, but there are also imaging methods where only a sub-set of the transducer elements in an array is receiving RF signals at any given time.

In a useful embodiment, the input to the NN are time-aligned RF signals, i.e. the time-shifted RF signals or the RF signals after time-of-flight correction, wherein the delays applied in the time-of-flight correction are relative to the transducer geometry. Such time correction may be done in the same way as in DAS beamforming. Preferably, the method operates in the time domain, i.e. on the signals in the time domain. To generate time-aligned RF signals, which may form the input for the NN, according to a useful embodiment, pixel-wise time-of-flight correction is applied to the RF signals as received (the raw RF signals). This results in a data array of size N, where N corresponds to the number of contributing transducer elements. Accordingly, the method may additionally comprise a step of performing time-of-flight correction on the signals to generate time-aligned signals.

The RF signals, also referred to as channel data, are fed into a trained artificial neural network, also termed "neural network" or NN. An artificial neural network (NN) is based on a collection of connected artificial neurons also called nodes, wherein each connection (also called edge) can transmit a signal from one node to another. Each artificial neuron receiving a signal may process it and transfer it to further artificial neurons connected to it. In useful embodiments, the artificial neurons of the inventive NN are arranged in layers. The input signals (e.g. the time-aligned RF signals) travel from the first layer, also termed the input layer, to the last layer, the output layer. In useful embodiments, the NN is a feed-forward network, although it may also be part of or may be a recurrent neural network, so that it can memorize its internal state and use it in the processing of a sequence of related inputs. In useful embodiments, the NN is trained on the basis of machine learning techniques, in particular deep learning, for example by back propagation. The training data used may be the output of a high-quality adaptive beamforming algorithm, such as the MV beamformer as a training target, and the related time-aligned RF signals as input training data. In useful embodiments, the invention uses a model-based approach to the NN architecture designed, taking on the structure of an adaptive beamformer, while performing computationally demanding calculations using a neural network.

The trained artificial neural network according to the invention may be provided in the form of a software program, but may also be implemented as hardware. Further, the trained NN may be provided in the form of a trained function which is not necessarily structured exactly in the same way as the neural network which was trained—for example, if certain connections/edges have the weight 0, after training, such connections may be omitted when providing the trained function, which is based on the trained artificial NN.

After training, the use of the inventive NN proved to result in higher quality images that approximate, if not improve over, the result of an MV beamformer, yet at a fraction of the computation time. According to current experiments, the time gain is approximately a factor of 500. Accordingly, the invention provides an extremely high-quality adaptive beamforming method, which provides the same quality as known adaptive beamforming algorithms such as MV beamformer, but at a fraction of the computation costs. Therefore, the inventive method allows to obtain much better quality of ultrasound images in real time. Accordingly, the invention provides image quality comparable to adaptive beamforming techniques, but at high rates, while using conventional and/or GPU accelerated hardware.

According to a useful embodiment, the number of input nodes of the artificial neural network and the number of output nodes of the artificial neural network corresponds to the number of contributing RF signals, wherein "contributing" means that the contributing RF signal is contributing to a respective beamformed output signal, e.g. a particular beamformed pixel. Accordingly, the number of input nodes N corresponds to the number of receiving ultrasound transducer elements, which may be all of the transducer elements in a transducer array, or a subset thereof. Preferably, each output node furnishes the content-adaptive apodization weight for one RF signal fed to one particular input node. Accordingly, in most embodiments, the number of input nodes will be identical or approximately identical as the number of output nodes of the NN.

In advantageous embodiments, in a next step, the content-adaptive apodization weights determined by the NN are applied to the RF signals—i.e. the same RF signals that are fed to the NN—to calculate a beamformed output signal. This may be done by a second connection which is added from the input (e.g. the time-aligned RF signals) to the multiplication and summation element where signal-wise the multiplication is performed between each of time-aligned said RF signals and each of the apodization weights which appear at the output of the NN. The beamformed output signal is preferably the RF signal corresponding to a pixel in an ultrasound image of the field-of-view. Accordingly, in useful implementations, the time-aligned RF signals corresponding to one pixel after another will be propagated through the neural network, and the same RF signals, weighted with the content-adaptive apodization weights, are summed to yield the beamformed output signal pixel-by-pixel. The beamformed output signal may be further processed to yield the respective pixel value by further method steps known in the art, in particular envelope detection.

In useful embodiments, the method comprises a step of receiving raw RF signals acquired by multiple ultrasound transducer elements from a field-of-view in response to an ultrasound transmission, followed by time-of-flight correction, to generate the time-aligned RF signals. Such time-of-flight correction may be done in accordance with methods known in the art, for example, as described in the dissertation by I. K. Holfort, *Adaptive Beamforming for Medical Ultrasound Imaging*, PhD Thesis, Technical University of Denmark, Lyngby, November, 2009. The time-aligned RF signals typically may have a frequency in the range of 1-50 MHz. The sampling rate of the signals acquired by the transducer elements will typically be higher than 50 MHz, for example at 100-400 MHz, typically 200 MHz.

According to a useful embodiment, the inventive method is a computer-implemented method for adaptive beamforming of ultrasound signals, the method comprising the steps of
a) Receiving raw RF signals acquired by an array of ultrasound transducers from a field-of-view in response to an ultrasound transmission;
b) Performing time-of-flight correction on the raw RF signals to generate time-aligned RF signals;
c) Determining content-adaptive apodization weights for beamforming the time-aligned RF signals by applying a trained artificial neural network to the time-aligned RF signals;
d) Applying the content-adaptive apodization weights to the time-aligned RF signals to calculate a beamformed output signal.

The neural network preferably comprises several layers, including hidden layers, and is thus preferably a deep network. The values of the nodes of the $(N+1)^{th}$ layer are calculated based on the values of the nodes of the $N^{th}$ layer. This may be done by multiplying the value of each node in the $N^{th}$ layer with the associated weight (not to be confused with the apodization weights) of the respective connection/edge, and adding it to one or several nodes in the $(N+1)^{th}$ layer. This operation is equivalent to a matrix multiplication. A fully-connected layer can be defined by the fact that a majority, in particular, all edges between nodes of the fully-connected layer and the nodes of the following layer or the preceding layer are present, and wherein the weight of each of the edges can be adjusted individually. Further, a bias may be added to the value of each node of a layer, and wherein the bias is also a trainable parameter.

In a preferred embodiment, the artificial neural network comprises at most four fully-connected layers. In some embodiments, even two or three fully-connected layers may be sufficient. The inventors have discovered that a relatively small neural network, thus needing only little computational effort, is sufficient to achieve excellent results. For example, there may be a fully-connected input layer and one or two fully-connected hidden layers, with a fully-connected output layer. Alternatively, there may be a fully-connected input layer and two or three fully-connected hidden layers wherein the last fully connected hidden layer directly connects to the output layer. In useful embodiments, the NN comprises at most two or three fully-connected hidden layers.

In useful embodiments, the NN will also include activation layers, which are preferably arranged between the fully-connected layers. An activation layer is one that applies a nonlinear function (termed "activation function" or "transfer function") to the value of each node and propagates the output of said activation function to the corresponding node in the following layer. In some nomenclatures, the activation function is not called layer, but considered part as another layer (i.e. a fully-connected layer), but in this document, it shall be termed "activation layer".

In useful embodiments, the artificial neural network comprises at least one activation layer including an activation function which propagates both positive and negative input values with unbounded output values. By "unbounded" it is meant that the output value of the activation function is not limited to any particular value (such as +1 or −1). Preferably, any value may in principle be obtained, thereby preserving the dynamic range of the RF signals. An example of such a function may be the Antirectifier function or the Concatenated Rectifier Linear Unit (CReLU), as described in the article by Shang et al., "Understanding and Improving Convolutional Neural Networks via Concatenated Rectifier Linear Unit", *Proceedings of the $33^{rd}$ International Conference on Machine Learning*, New York, USA, 2016.

Because of the large dynamic range of the RF signals fed to the NN, which in addition have both positive and negative components, traditional activation functions, such as the hyperbolic tangent and the Rectifier Linear Unit (ReLU), are not well suited for the application of the invention. The ReLU avoids vanishing gradients due to its positive unbounded output. Such a non-linearity may however not be appropriate when dealing with RF input data, as it inherently leads to many dying nodes, impairing the training process. In contrast, the hyperbolic tangent activation is able to preserve negative values. It is however bounded between −1 and 1, and therefore tends to saturate quickly for signals with a large dynamic range, resulting in a vanishing gradient during back propagation. Instead, in useful embodiments, the invention uses an activation function which introduces non-linearity, while preserving negative signal components as well as the dynamic range of the signal. Accordingly, using such activation function improves the quality of the beamformed output image. Further, a neural network can be designed accurately reproducing adaptively beamformed target images while having minimal network size.

In a further useful embodiment, the neural network comprises at least one activation layer including an activation function which concatenates the positive and negative part of the input values, wherein "input values" mean the values fed to the activation layer, i.e. the values of the nodes of the activation layer. Accordingly, negative and positive values are propagated into different nodes in the next layer, wherein the value of at least one of these two nodes is zero. Consequently, the number of nodes of the next layer is twice as high as the number of nodes in the activation layer. In other words, the output of the activation layer will have twice the size of the input. In useful embodiments, the output will always be positive, which has the advantage that the activation preserves the energy information, i.e. it keeps the module of the signal, but also preserves both positive and negative signal information. In useful embodiments, the activation function may be an Antirectifier function, which combines a sample-wise L2 normalization with two ReLU activations, thereby concatenating the positive and the negative part of the input, as described in F. Chollet, "Antirectifier," *GitHub,* 2018. [Online]. Available: https://github.com/keras-team/keras/blob/4f2e65c385d60fa87bb143c6c506cbe428895f44/examples/antirectifier.py. This Antirectifier operation may be described as $$f(x) = \begin{bmatrix} \max\left(0, \frac{x-\mu_x}{\|x-\mu_x\|}\right) \\ \max\left(0, -\frac{x-\mu_x}{\|x-\mu_x\|}\right) \end{bmatrix}.$$

where $\mu_x$ is the mean of the vector or batch of input values propagated through the activation layer at any one time, and $\|x-\mu_x\|$ is the L2 norm or variance. Accordingly, the activation function preferably applies L2 normalisation before activation. This normalisation allows the activation to operate more symmetrically on the signal. Further, the L2 normalisation has the advantage that the training converges more quickly.

According to a useful embodiment, the artificial neural network comprises at most three activation layers. In useful embodiments, an activation layer is placed between two fully-connected layers, preferably an activation layer is placed between each pair of fully-connected layers, i.e. after each of the fully-connected layers except the last (which preferably connects directly to the output layer).

In useful embodiments, the beamformed output signal is used to reconstruct an ultrasound image of a field-of-view, wherein the signals, preferably time-aligned RF signals, are rearranged prior to applying the trained artificial neural network, so that the RF signals (RF data) relating to one or at most a few pixels of the ultrasound image are processed in one or more batch(es) by the NN. If a vector is a set of values fed into an input layer of NN at the same time, a batch will be a sequence of such vectors, which together includes all of data required to reconstruct one (or several) pixels in the beamformed ultrasound image. In other words, the NN may be arranged to output the apodization weights pixel-by-pixel. In order to do this, in some implementations it is useful to re-arrange the time-aligned RF signals, such that the RF signals contributing to each pixel are put behind one another, so that each pixel may be processed independently. Each batch of data fed into the NN relates to one (or at most a few) specific pixel(s), wherein some parts of the RF signals may be duplicated in the rearranging because they contribute to several pixels.

In a preferred embodiment, the RF signals relating to one single pixel of the ultrasound image are processed in one batch by the NN, whereby the number of input nodes corresponds to the number of the RF signals contributing to said one pixel.

In another embodiment, the NN is extended to increase its field-of-view by also incorporating neighbouring pixels in the beamforming process. Thereby, the RF data relating to several neighbouring pixels, for example up to 9, are processed in one batch by the neural network. Accordingly, the number of input nodes of the NN is increased. This embodiment improves clutter suppression, thus increasing image quality further, however at the expense of higher hardware requirements because of the increased network size. The several neighbouring pixels may be neighbouring to each other in any direction, i.e. in the plane of the ultrasound image or across imaging depth.

In another embodiment, the artificial NN comprises at least one convolutional layer, in addition to or as an alternative to one or several fully-connected layers. Such convolutional layers may be applied either across the time-aligned RF signals, or may be applied across input space. A convolutional neural network usually comprises at least a convolutional layer and pooling layer, wherein a kernel is applied to the convolutional layer. The kernel operation is performed on a sub-set of the nodes of the convolutional layer, and the output is propagated to one node in the pooling layer. Usually, within a convolutional neural network the nodes of the convolutional layer can be considered to be arranged as a d-dimensional matrix, such as a d-dimensional image. The advantage of using convolutional layers is that especially local correlation of the input values can be exploited by enforcing a local connectivity pattern between nodes or layers, in particular by each node being connected to only a small region of the nodes of the preceding layer.

Accordingly, the use of convolutional layers reduces the amount of trainable parameters and speeds up both training and prediction. In a useful embodiment, one of the fully-connected layers is replaced by a convolutional layer (and possibly a subsequent pooling layer). In another useful embodiment, all hidden layers are convolutional layers (possibly followed by pooling layers).

In a further useful embodiment, the NN is or is part of a recurrent neural network (RNN). In a recurrent network, the feedback is creating a memory function, thereby giving the network a memory property. Such memory function can be useful in processing sequences of related data, such as real-time ultrasound images, wherein the transducer is slowly moved over the imaged body part, so that the field-of-view of the ultrasound image is not completely changed from one image to the next. In a useful embodiment, the RNN has several layers, wherein at least one of the hidden layers is connected to a set of context nodes using a fixed weight of one. At each time step, the input is fed-forward through the layers. The fixed back-connections save a copy of the previous values of the hidden nodes in the context nodes. Thus, the network can maintain a sort of state, allowing it to perform such tasks as sequence-prediction that are beyond the power of a standard feed-forward NN. According to useful embodiments, some or all of the weights of the artificial neural network are quantized, in particular quantized to 1 to 4 bits. Thus, the weights are rounded to one of a limited number of possible values, e.g. one of 2 values (0 and 1), or one of 4 or 8 values. Thereby, the memory and processing requirements of the NN are reduced. In a useful example, the weights are quantized to 1-bit such that they can only adopt a binary value. This embodiment is very advantageous for memory constraint implementations such as on a Field Programmable Gate Array (FPGA). Surprisingly, it has been shown that good results can be obtained even if the weights are thus limited in memory size.

In useful embodiments, the trained neural network of the invention may be part of a larger neural network, which completely processes the RF signals acquired from ultrasound transducers, for example to finally generate the reconstructed image or provide analysis data on the image. Preferably, the trained neural network of the invention is that part of the larger neural network, which provides the apodization weights useful in content-adaptive beamforming.

According to a useful embodiment, the trained neural network of the invention comprises at least one hidden layer having fewer nodes than the input layer and/or the output layer of the artificial neural network, for example by a factor of 2-32, preferably by a factor of $2^2$ to $2^4$ fewer nodes. In useful embodiments, all of the hidden fully-connected layers have fewer nodes than the input and output layers. This dimensionality reduction forces the network to find a more compact representation of the data which helps in noise suppression. For example, the first hidden fully-connected layer may have a factor of 2-16, preferably 4-8 fewer nodes than the input layer.

According to a further aspect, the invention provides a method for providing a trained artificial neural network useful in content-adaptive beamforming of ultrasound signals, the method comprising: (a) Receiving input training data, namely RF signals, e.g. time-aligned RF signals, acquired by multiple ultrasound transducer elements in response to an ultrasound transmission, (b) Receiving output training data, wherein the output training data are content-adaptive apodization weights, wherein such content-adaptive apodization weights have been calculated from the RF signals by a content-adaptive beamforming algorithm, in particular a minimum variance algorithm, or wherein the output training data are beamformed output signals calculated from the RF signals by a content-adaptive beamforming algorithm; (c) training an artificial neural network by using the input training data and the output training data; and (d) providing the trained artificial neural network.

Accordingly, in a first embodiment the NN is trained using beamformed RF signals as a training target. These target signals should be representative for the desired quality and characteristics of the signals that are produced when using the trained NN (e.g. having high spatial resolution, minimal clutter or maximum contrast). These target signals can originate from a numerical simulation that provides input signals and associated beamformed output signals. Alternatively or additionally, these input signals can originate from captured RF signals that have been processed with a beamforming algorithm that is known to provide beamformed output signals with a desired quality and with known desired characteristics. This beamforming algorithm can be a content-adaptive beamforming algorithm, in particular a minimum variance beamforming algorithm. The NN is then arranged to calculate apodization weights in a content adaptive fashion. In this embodiment, preferably a constraint that the apodization weights add up to 1 is used during training, such that any deviation from 1 is penalized by adding to the cost function.

In a second embodiment, the NN is trained by providing content-adaptive apodization weights as a training target, which have been calculated using a known content adaptive beamforming algorithm, such as the Minimum Variance algorithm. These known techniques are typically data-dependent beamforming methods that seek to adaptively process the available channel data in order to suppress off-axis clutter, and/or yield a lateral resolution beyond the diffraction limit. Other known adaptive beamforming techniques include nonlinear inversion schemes enforcing sparsity in a specified domain (as used in compressive sensing), amplitude and phase estimation (APES) and aperture domain model image reconstruction (ADMIRE). However, these algorithms are computationally very expensive and therefore can only be used on the training data, not on the actual real-time image data. For example, for minimum variance beamforming, a matrix inversion has to be performed for every pixel in the image.

The artificial neural network may be arranged as described above, i.e. it may be a deep network having several layers, preferably up to four fully-connected layers and up to three activation layers. The training may be done by backpropagation. In this method, the time-aligned RF signals are propagated through the NN using predetermined weights of the edges. The output is compared to the output training data using an error- or cost-function, the output of which is propagated back through the NN, thereby calculating gradients to find the network weights (and possibly other parameters such as bias) that yield minimum errors. This may be done by adjusting the weights of the edges and following negative gradients in the cost function. It has been found that the weights of the neural network, according to the invention, converge very quickly to a minimum, so that the NN can be trained on a very limited number of data, relating to only one or few ultrasound images.

In useful embodiments, the neural network uses drop-out layers during training. Thereby, certain nodes/connections in the drop-out layer are randomly selected and the values/weights are set to 0. For example, a drop-out layer may have a pre-determined percentage of drop-out nodes such as 30-80%, e.g. 50% of all nodes are dropped-out and their values/weights set to 0. For the next backpropagation of training data, a different set of nodes in the drop-out layer is set to 0. This creates noise during training but has the advantage that the training converges to a useful minimum. Accordingly, the NN is much better trainable when using drop-out layers. In useful embodiments, one, two or three fully-connected layers are followed by drop-out layers during training. By using drop-out layers, the number of connections are reduced, and during each iteration of the back propagation, only a sub-network is trained. However, the actual network in use is the full NN (without any drop-out layers).

It is further useful during training, if the artificial neural network comprises at least one activation layer including an activation function using L2 normalisation. This will cause the training will to converge more quickly.

According to a further embodiment, the apodization weights produced by the NN are constrained by implementing a cost function (also referred to as loss function) penalizing deviations from unity gain. Thus, the neural network produces apodization weights, of which the sum is close to 1. In useful embodiments, this is not strictly enforced during training of the neural network, but any deviations from the sum of one is penalised by adding to the cost function.

Accordingly, the invention advantageously provides a robust beamformer that produces an output signal that remains proportional to the input.

Preferably, the trained artificial neural network used in determining content-adaptive apodization weights is trained with the above method. Further preferably, the trained artificial neural network of the inventive method is provided by the above training method.

The invention is also related to a computer program comprising instructions, which, when the program is executed by a computational unit, causes the computational unit to carry out the adventive method. This is true for both of the adaptive beamforming method and the training method. Alternatively, the neural network may be implemented as hardware, for example with fixed connections on a chip or other processing unit. The computational unit, which may execute the inventive method, may be any processing unit such as a CPU (Central Processing Unit) or GPU (Graphics Processing Unit). The computational unit may be part of a computer, a cloud, a server, mobile device such as a laptop, tablet computer, mobile phone, smartphone etc. In particular, the computational unit may be part of an ultrasound imaging system.

The invention is also directed to a computer-readable medium comprising instructions which, when executed by a computational unit, causes the computational unit to carry out the method according to the invention. Such computer-readable medium may be any digital storage medium, for example a hard disk, a server, a cloud server, an optical or a magnetic digital storage medium, a CD-ROM, a SSD-card, an SD-card, a DVD or an USB or other memory stick.

According to another aspect, the invention is also related to a system for adaptive beamforming ultrasound signals, the system comprising a) a first interface, configured for receiving RF signals acquired by multiple ultrasound transducer elements in response to an ultrasound transmission; b) a computational unit configured for applying a trained artificial neural network to the RF signals, whereby content-adaptive apodization weights for beamforming the RF signals are generated, and for applying the content-adaptive apodization weights to the RF signals to calculate a beamformed output signal; c) a second interface, configured for outputting the beamformed output signal.

The system is preferably configured to execute the inventive method for adaptive beamforming of ultrasound signals. Such a system may be implemented on an ultrasound imaging system, e.g. it is implemented on one of its processing units such as a GPU. However, it is also conceivable that the RF signals acquired by the ultrasound transducer of an ultrasound imaging system are transferred to another computational unit, local or remote, for example via the internet, and the adaptive apodization weights are transferred back from there and used in calculating the beamformed output signal.

Further, the invention is also directed to a system for training an artificial neural network by the inventive training method.

According to a further aspect, the invention is directed to an ultrasound imaging system comprising an ultrasound transducer array configured to transmit and receive ultrasound signals; a plurality of channels operatively coupled to the ultrasound transducer array configured to transmit channel data, also termed RF signals, based at least in part of the received ultrasound signals; a beamformer operably coupled to the plurality of channels, wherein the beamformer is configured to time-align the channel data; and a signal processor operatively coupled to the beamformer, wherein the signal processor is configured to perform the method according to any of claims 1-12. Due to the low computational cost of said method, such a signal processor can be integrated into existing ultrasound systems.

SHORT DESCRIPTION OF THE FIGURES

Useful embodiments of the invention shall now be described with reference to the attached figures. Similar elements or features are designated with the same reference signs in the figures. In the figures.

DESCRIPTION OF EMBODIMENTS

Figure 1:
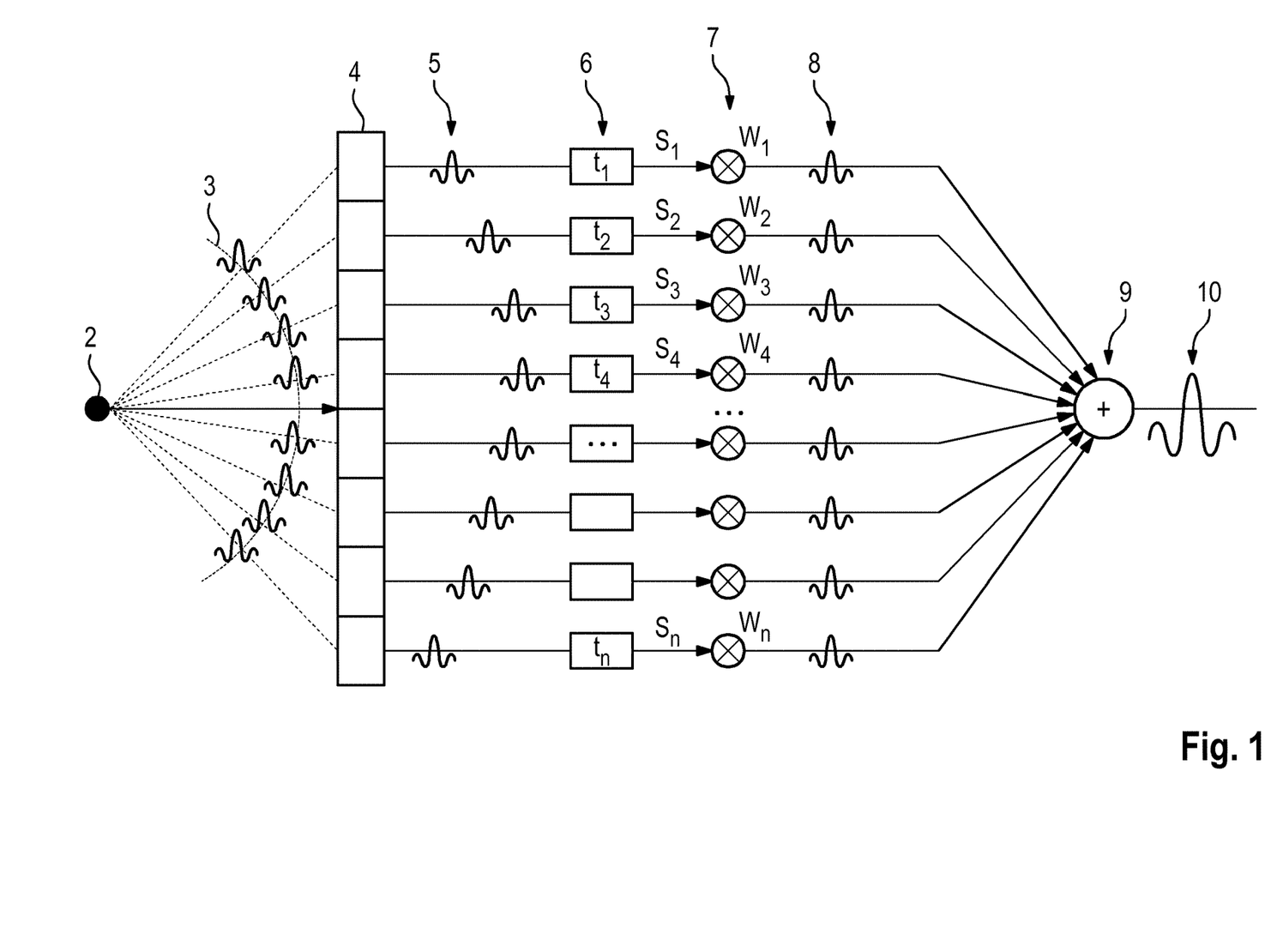
FIG. 1 is a schematic illustration of a conventional DAS beamforming technique.

FIG. 1 illustrates conventional beamforming with the delay-and-sum (DAS) method. In response to e.g. an ultrasound pulse transmitted by an array 4 of transducer elements, echoes 3 are reflected from a point structure (focal point) 2 in the field-of-view. The echoes 3 are recorded by the array 4 of ultrasound transducers. The thus acquired raw RF signals 5 are also referred to channel data, each raw RF signal 5 having been acquired by one transducer element and thus relating to one channel. The example in FIG. 1 shows 8 channels. For beamforming, the channel data 5 are time-of-flight corrected in step 6, i.e. the different time shifts $t_1$, $t_2$, ..., $t_n$ in which the echoes 3 were acquired by the array 4 are corrected for, depending on the geometry of the transducer array 4 and the focal point 2. These time-aligned RF signals $S_1$ ... $S_n$ are then multiplied with apodization weights $w_1$ ... $w_n$ in step 7. In conventional DAS-beamforming, these weights are pre-set and not adapted to the content of the ultrasound image, i.e. they are not adapted to the RF signals. The weighted signals 8 are summed in step 9, to yield a beamformed output signal 10. This beamformed output signal 10 can be further processed to yield image data for one pixel.

Figure 2:
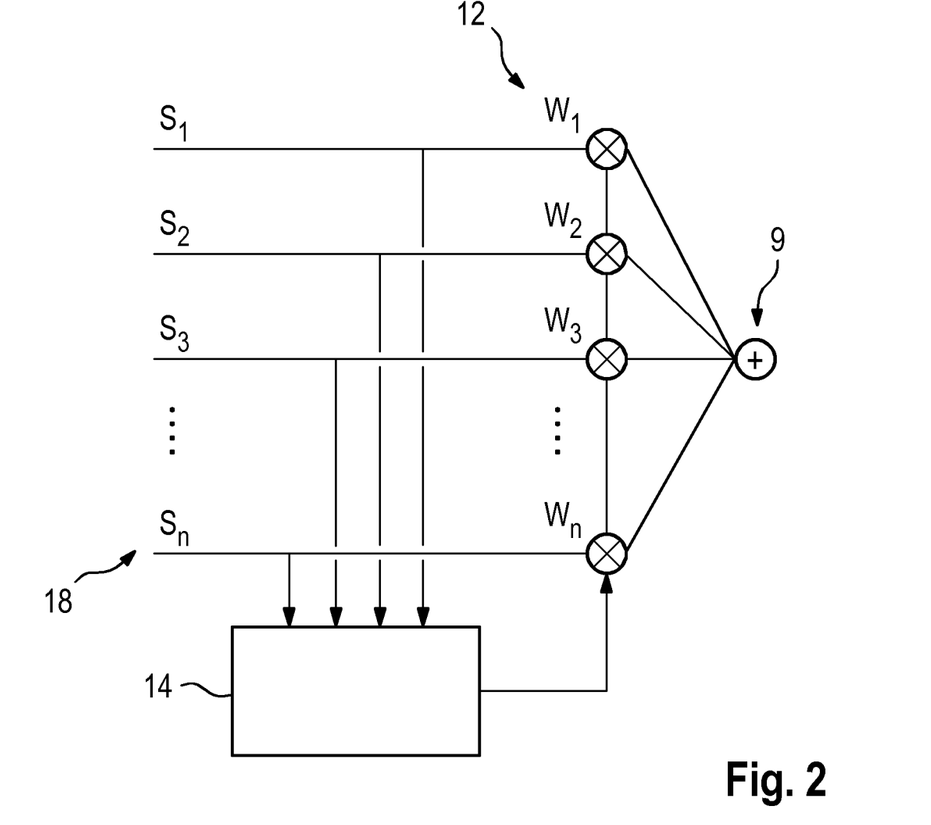
FIG. 2 depicts a schematic overview of an adaptive beamformer.

FIG. 2 shows an adaptive beamforming method. In this method, the time-aligned RF signals 18 $S_1$, $S_2$ ..., $S_n$ are used by a beamforming algorithm 14 to calculate the content-adaptive apodization weights 12, which, thus, are not pre-determined as in the DAS-beamformer. Rather, the signals are processed by the adaptive beamformer 14, e.g. a minimum variance beamformer, which calculates the optimal weights in order to maximize image quality. The weighted RF signals are summed in step 9, which results in the beamformed output signal.

Figure 3:
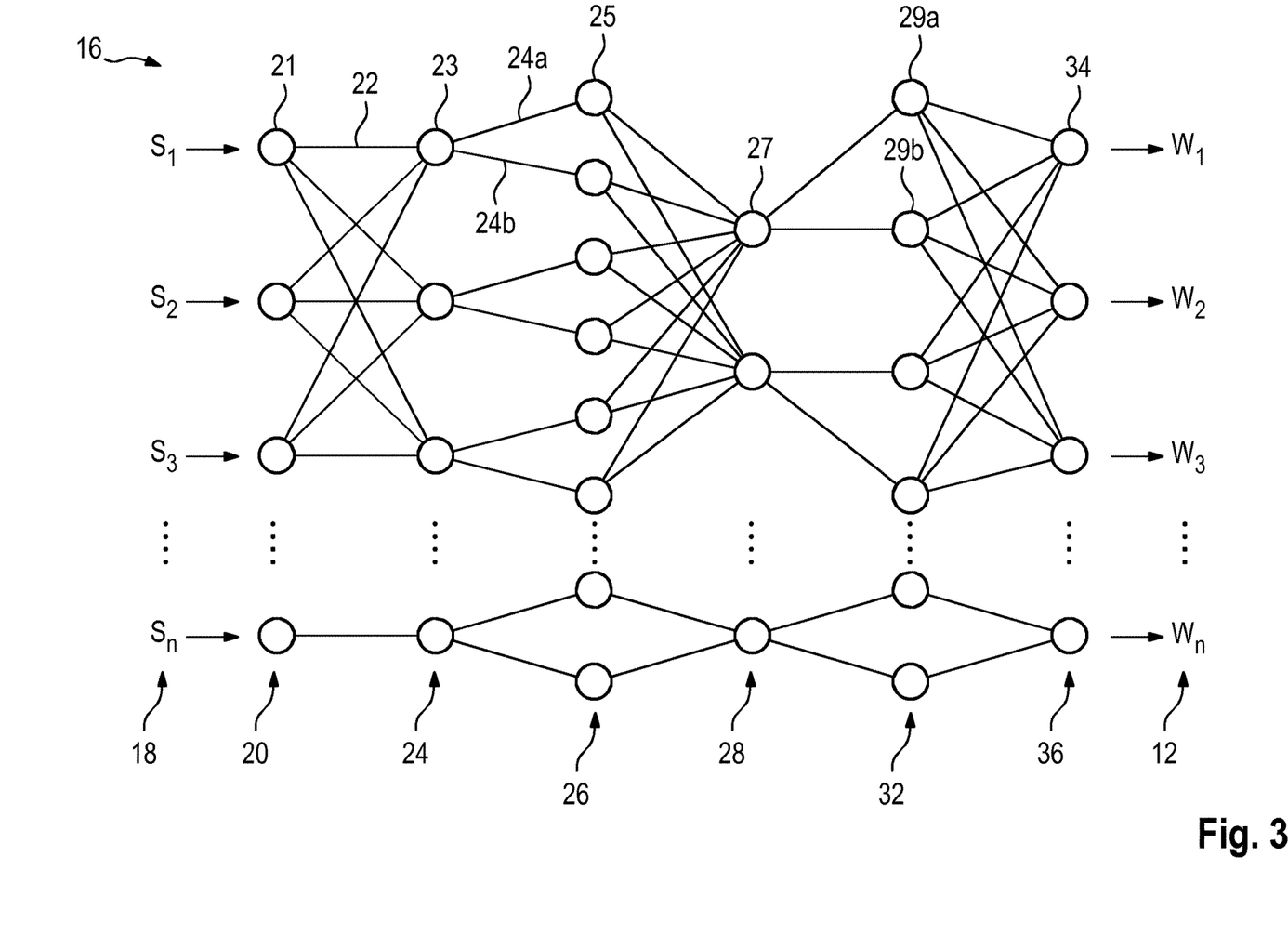
FIG. 3 is a simplified illustration of a neural network, according to an embodiment of the invention.

According to the invention, the conventional adaptive beamforming algorithm/processor 14, is replaced by a neural network. An example of such neural network 16 is shown in FIG. 3. This example network is arranged into layers 20, 24, 26, 28, 32, 36, each layer consisting of a number of nodes, wherein the nodes between neighbouring layers are connected by edges. Each edge/connection corresponds to a simple operation, which is performed on the value of the first node, and the value of this operation is added to the value of the connected node. In particular, a real or complex number can be assigned as a value to each node of the neural network.

The neural network 16 receives as input the time-aligned RF signals 18 $S_1, S_2 \ldots, S_n$ acquired from a plurality of ultrasound transducers, and which are to be used to calculate one pixel. The number of nodes 21 in the input layer 20 corresponds to n, the number of contributing RF signals. In this embodiment, the number n of nodes 34 of the output layer 36 corresponds to the number n of nodes 21 of the input layer 20. To calculate the content-adaptive apodization weights $w_1, \ldots, w_n$, the input values signals $S_1, S_2 \ldots, S_n$ are propagated through the neural network.

In this embodiment, the input layer 20 is a fully-connected layer, i.e. each node 21 in the input layer is connected by an edge 22 with each node 23 in the next layer 24. This operation corresponds to a matrix multiplication, wherein each value of the input layer 20 is multiplied with the weights of the edges connecting it to the nodes 23 in the next layer 24.

The next layer is an activation layer 24, in this example an antirectifier layer. The antirectifier effectively introduces non-linearity, while preserving negative signal components as well as the dynamic range of the input. Because it concatenates the positive and the negative part of the input, in effectively doubles the number of nodes 25 in the following layer 26, since each node 23 has a different output depending on whether it has a positive or a negative input value, as illustrated by the two edges 24a and 24b. Otherwise, the structure of the nodes 25 contained in the following layer 26 is equivalent to the structure of the nodes 23 in the activation layer 24, i.e. there is no inter-connection between neighbouring nodes 23 in layer 24.

The layer 26 following the activation layer 24 is again a fully-connected layer, i.e. each node 25 in this layer is connected to each node 27 in the following layer 28. This following layer 28 has significantly fewer nodes 27 than the preceding layer 26. By reducing the number of nodes, the number of parameters/weights that needs to be trained is reduced. This leads to the amount of computation in the network being reduced and to a control of overfitting. For example, there may be a dimensionality reduction by a factor of 3-6, in the shown example, the factor is 3, i.e. the layer 28 has a third of the size of the preceding layer 26. In useful embodiments, the factor will be 5. The layer 28 is again an activation layer, namely an anti-rectifier layer, which combines a sample wise L2 normalisation with two ReLU activations, thereby concatenating the positive and the negative part of the input. This results in a doubling of the number of nodes 29 in the next layer 32. This layer 32 is again a fully-connected layer, since each node in layer 32 is connected to each node 34 in the output layer 36. The values outputted at output layer 36 are the content-adaptive apodization weights $w_1, \ldots, w_n$.

In the embodiment of FIG. 3, the neural network has three fully-connected layers (the output layer 36 not counting as one, since it does not propagate any values to a following layer), wherein the fully-connected layers are named 20, 26 and 32. Further, the network has two activation layers 23 and 28, each in between a pair of fully-connected layers. In other useful embodiments, there may be another fully-connected layer followed by an activation layer, i.e. a total of 4 fully-connected layers and three activation layers.

Figure 4:
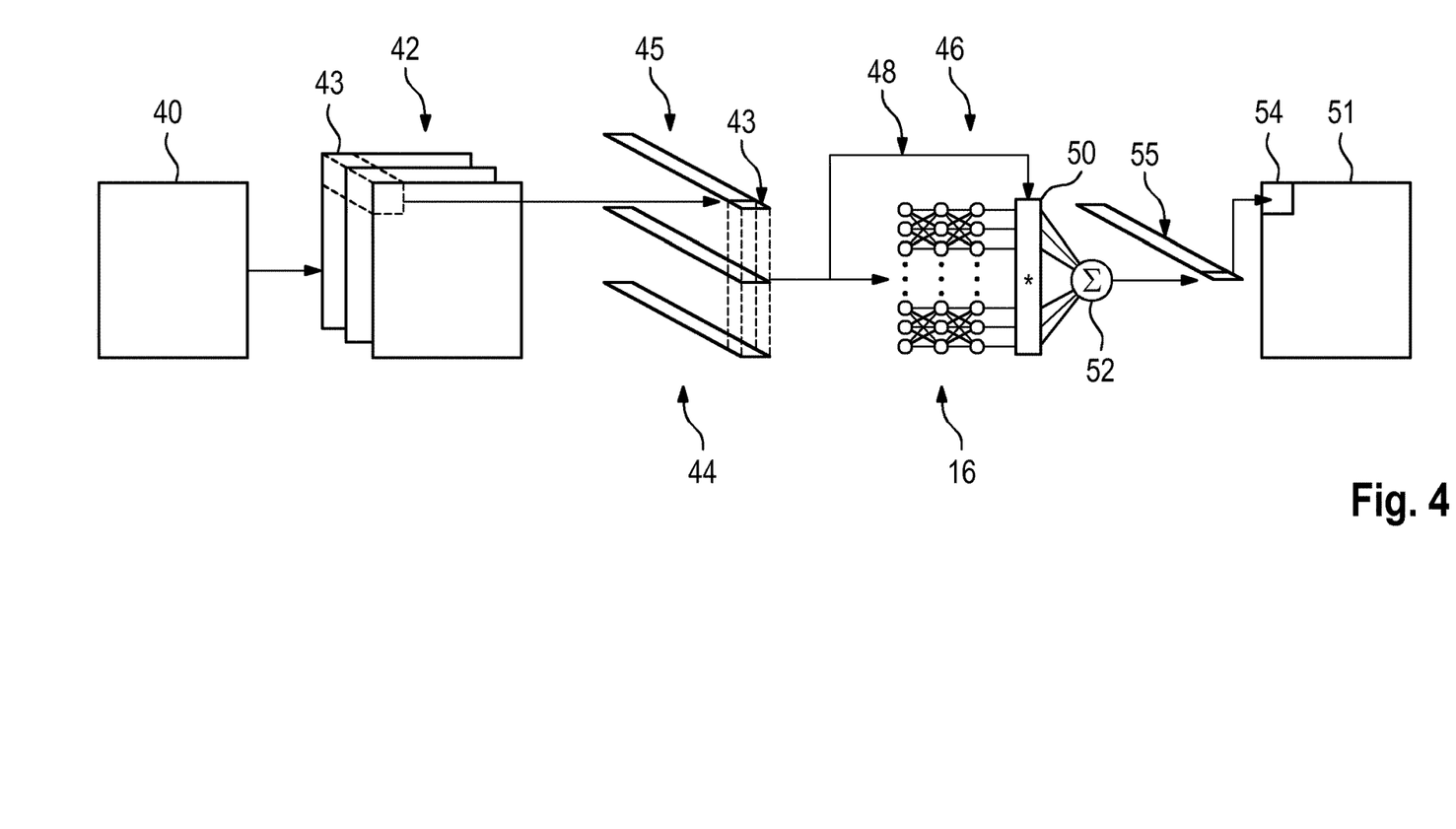
FIG. 4 is a schematic overview of an implementation of an embodiment of the inventive method.

In FIG. 4, a schematic overview of a possible implementation of the inventive method is given. The (raw) RF signals are illustrated as input data at 40, wherein the data comprises of a number of channels, each having a number of axial samples. In step 42, the raw RF data is time-aligned using traditional methods, wherein the different planes stand for the data of the different channels. In this embodiment, the time-of-flight correction of the RF signals is calculated beforehand and stored in a buffer. Alternatively, the time-of-flight correction could also be computed on the fly in a GPU, thereby reducing communication and memory overhead. Further, in this implementation, all data 43 from the various channels relating to one pixel is rearranged into a new format 45 in step 44, so that the data 43 for each pixel can be processed as a single batch in the NN. The next step of applying the NN 16 to the time-aligned and rearranged RF signal 45 is shown at 46. A skip connection 48 is added from the input (time-aligned RF signals) to the output at 50, where the time-aligned RF signals are multiplied with the apodization weights generated by the NN in step 52. The result is beamformed RF data 55 relating to one pixel 54, which is used to reconstruct an ultrasound image 51. After beamforming by the NN, the beamformed pixels are rearranged according to their spatial location.

Figure 5:
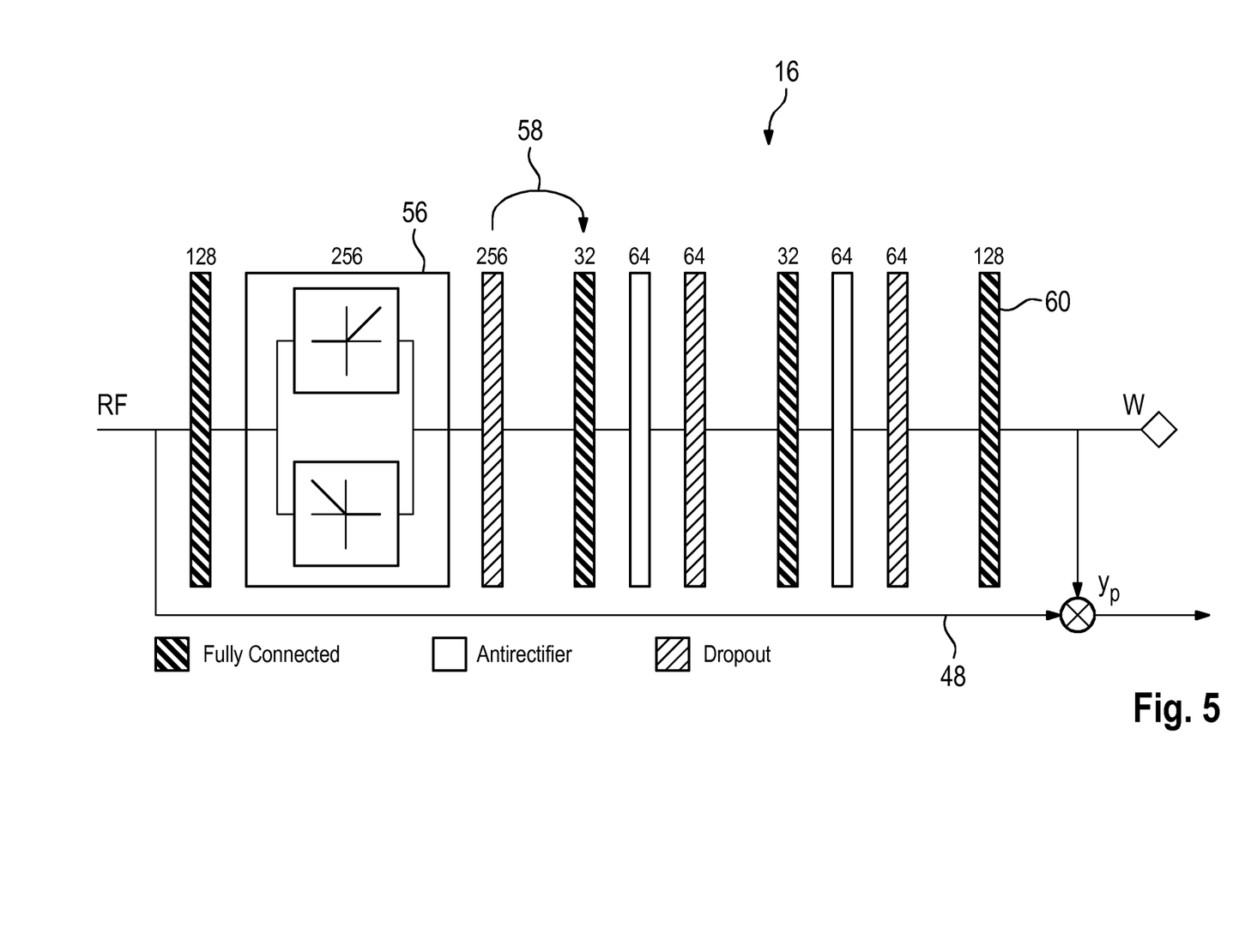
FIG. 5 shows a schematic representation of an artificial neural network, according to an embodiment of the invention.

The neural network 16 of this preferred embodiment is shown in more detail in FIG. 5. Above each layer its output size (for 128 contributing RF signals) is indicated. The fully-connected layers are illustrated by a dark shading, the antirectifier layers are illustrated in white, and the drop-out layers (which are only present during training of the network) are illustrated in a light shading. This NN 16 comprises four fully-connected layers comprising 128 nodes for the input layer and output layer, and 32 nodes for the inner layers. This dimensionality reduction 58 by a factor of 8 ($2^3$) following the first antirectifier layer, or by a factor of 4 with respect to the input layer, forces the network to find a more compact representation of the data. Each of the fully-connected layers (except the last layer) is followed by an Antirectifier layer. The last fully-connected layer 60 is either the output layer or is directly connected to an output layer (not shown).

During training, dropout is applied between each pair of fully-connected layers, for example with a probability of 0.2. In other words, during training a fixed percentage of the nodes in the dropout layers are dropped out. Thus, the dropout layers are present only during training the network. The dropout helps to reduce overfitting of the neural network to the training data.

The NN may be implemented in Python using the Keras API with a TensorFlow (Google, CA, USA) backend. For training the Adam optimizer was used with a learning rate of 0.001, stochastically optimizing across a batch of pixels belonging to a single image. The neural network shown in FIG. 5 was implemented and trained on in vivo ultrasound image data.

When training the neural network shown in FIG. 5, the apodization weights calculated by a known adaptive beamforming technique using traditional algorithms may be used as output training data. The input training data is the corresponding time-aligned RF signals. During training, the NN 16 is applied to the training input data to generate calculated output data. A comparison between the calculated output data and the output training data is used to recursively adapt the weights within the neural network 16, in this case at a learning rate of, for example 0.0005 to 0.01. To prevent overfitting, methods of regularization can be used, i.e. drop-out of nodes, using artificially calculated data or weight decay based on normalization.

Figure 6:
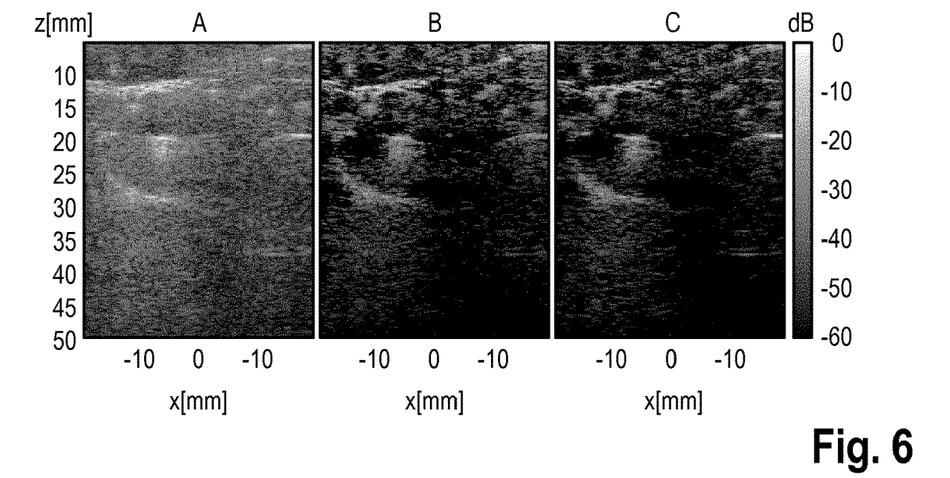
FIG. 6 shows ultrasound images obtained with (A) conventional DAS beamforming, (B) minimum variance beamforming, (C) a deep learning based beamformer according to an embodiment of the invention.

The NN of FIG. 5 was tested on images acquired using a single plane-wave transmission, and the results are shown in FIG. 6. The image designated A shows the image reconstructed with a DAS beamformer. The image B uses a minimum variance beamformer, and in image C the deep learning based beamformer according to the implementation of the invention was applied. It can be observed that the NN beamformer is able to generate a high-contrast image comparable to the MV target, with significantly less clutter. Further, both adaptive techniques show an increase in CNR (Contrast-to-noise ratio) and resolution compared to the DAS, with the NN even outperforming the MV target on the latter, likely due to its ability of incorporating a generable prior in the beamforming process by averaging statistics of the training data. Training on higher quality images allows for improving the performance of the NN even further.

The method according to this embodiment of the invention was also tested on simulated images in order to compare resolution and contrast. Resolution was assessed by evaluating the averages full-width-at-half-maximum (FWHM) of all point scatterers. Contrast was estimated using the average CNR of anechoic cysts. The results are shown in Table 1. Thus, the NN beamformer is able to generate a high contrast image, with significantly less clutter than the MV target.

TABLE 1

Resolution and Contrast metrics

| Parameter | DAS | NN | MV |
| --- | --- | --- | --- |
| $FWHM_{lat}$ (mm) | 0.846 | 0.704 | 0.778 |
| $FWHM_{ax}$ (mm) | 0.431 | 0.342 | 0.434 |
| CNR (dB) | 10.96 | 11.48 | 12.45 |

Figure 7:
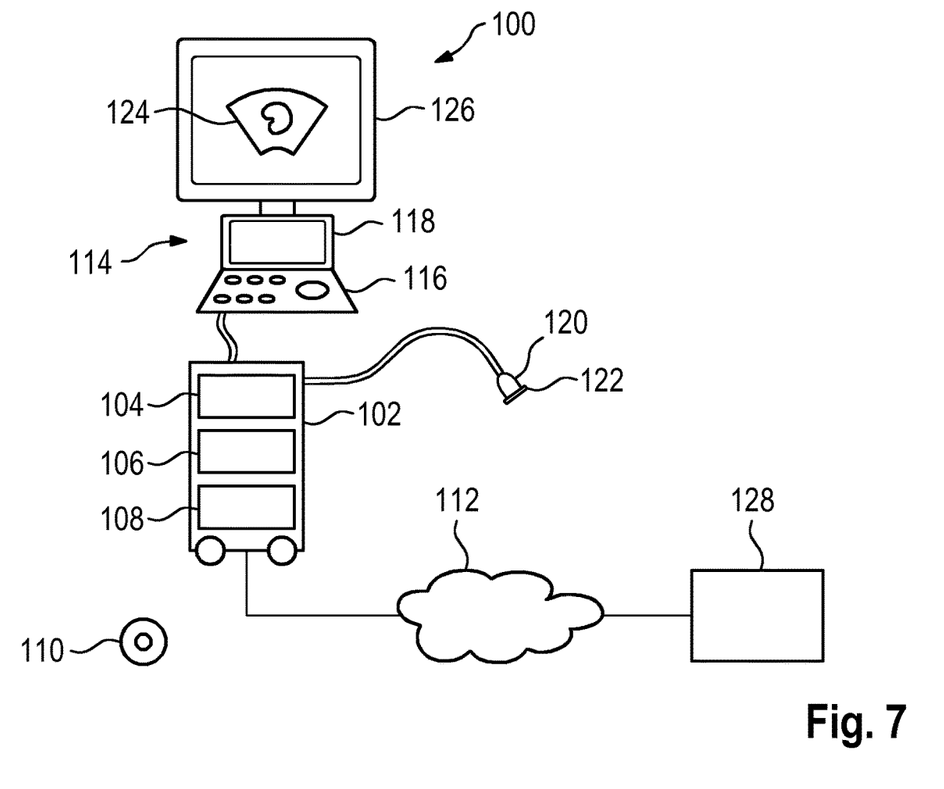
FIG. 7 shows an ultrasound imaging system according to an embodiment of the invention.

FIG. 7 is a schematic representation of an ultrasound system 100 according to an embodiment of the invention and configured to perform the inventive method. The ultrasound system 100 includes a usual ultrasound hardware unit 102, comprising a CPU 104, GPU 106 and digital storage medium 108, for example a hard disc or solid-state disc. A computer program may be loaded into the hardware unit, from CD-ROM 110 or over the internet 112. The hardware unit 102 is connected to a user-interface 114, which comprises a keyboard 116 and optionally a touchpad 118. The touchpad 118 may also act as a display device for displaying imaging parameters. The hardware unit 102 is connected to the ultrasound probe 120, which includes an array of ultrasound transducers 122, which allows the acquisition of live ultrasound images from a subject or patient (not shown). The live images 124, acquired with the ultrasound probe 120 and beamformed according to the inventive method performed by the CPU 104 and/or GPU, are displayed on screen 126, which may be any commercially available display unit, e.g. a screen, television set, flat screen, projector etc.

Further, there may be a connection to a remote computer or server 128, for example via the internet 112. The method according to the invention may be performed by CPU 104 or GPU 106 of the hardware unit 102 but may also be performed by a processor of the remote server 128.

Figure 8:
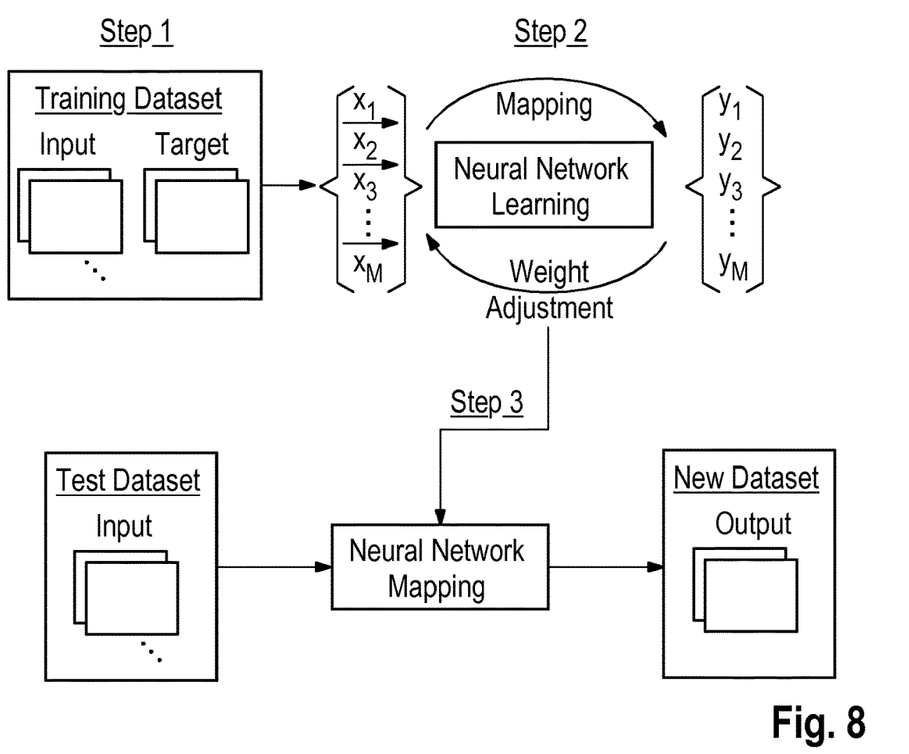
FIG. 8 shows an overview of an alternative neural network based beamforming method.
Figure 9:
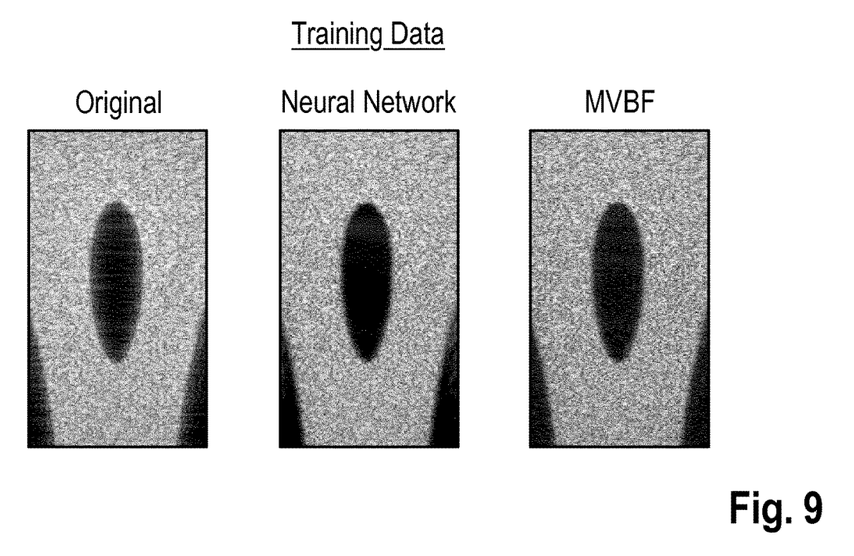
FIG. 9 shows a training data set from a simulated phantom used in the alternative method, wherein the original image is shown on the left, the image obtained by the alternative neural network method in the middle, and the minimum variance beamformed image on the right.
Figure 10:
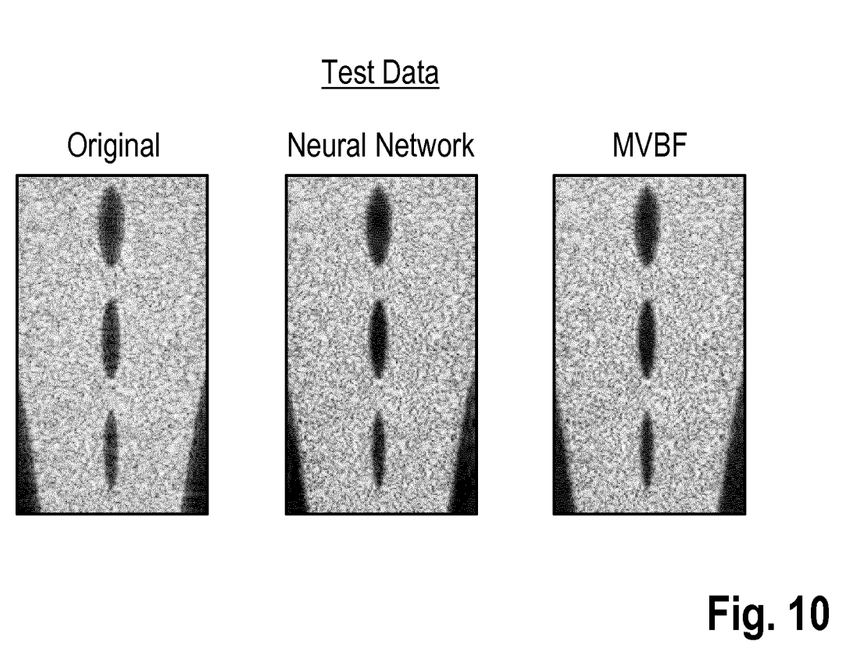
FIG. 10 shows a test data set from a simulated phantom pertaining to the alternative method, wherein the original image is shown on the left, the image obtained by the alternative neural network method in the middle, and the minimum variance beamformed image on the right.

FIGS. 8 to 10 relate to an alternative aspect of the invention, in which a NN is used not to calculate apodization weights, but outputs adaptively beamformed RF data. The aim of this alternative aspect may be described as learning the behaviour of a given adaptive beamforming (BF) algorithm more accurately, by learning the actual mathematical operations of the adaptive BF algorithm involving per-channel data (i.e. RF signals) and beamformed RF data, rather than just learning the effect of adaptive beamforming purely in image domain. This alternative aspect provides a machine learning framework involving multi-layer perceptrons (MLPs) to learn computationally expensive adaptive beamforming algorithms, such as the MV or other techniques described above. However, this machine learning framework is intended to learn the mapping between aligned complex per-channel data and the adaptively beamformed RF data as opposed to mapping between pixel values from original and adaptively beamformed images.

An MLP is a feedforward artificial neural network, which takes a set of input data and maps onto a set of appropriate outputs. An MLP consists of multiple layers of neurons, which have nonlinear activation functions, with each layer being fully connected to the next one. It has been demonstrated previously that the minimum number of layers needed to represent an arbitrary continuous mapping $y=f(x_1, x_2, \ldots, x_n)$ is 3, having the input layer, the hidden layer, and the output layer. A 3-layer MLP (or equivalently a 1-hidden-layer MLP) is a function $f: R^n \rightarrow R^l$, where n is the size of the input vector x and l is the size of the output vector $f(x)$ such that, in matrix notation:

$$y \approx f(x) = G\{b^{(2)} + W^{(2)}[s(b^{(1)} + W^{(1)}x)]\},$$

where $b^{(1)}$ and $b^{(2)}$ are bias vectors, $w^{(1)}$ and $w^{(2)}$ are weight matrices and G and s are activation functions. A commonly-used activation function is in the form of a sigmoid function:

$$g(z) = \frac{1}{1 + e^{-\lambda z}},$$

where λ determines the slope of the transition from 0 to 1. The weight matrices $w^{(1)}$ and $W^{(2)}$ are computed using a training algorithm such as the Levenberg-Marquardt or the backpropagation algorithms.

The neural networks used in this alternative aspect are first trained to learn an adaptive beamforming algorithm based on a training dataset that has been generated by Field II simulation and then, the trained neural network is applied to two different test datasets to prove the concept. The alternative aspect is a framework that can be generalized to many other computationally expensive adaptive beamforming techniques as long as sufficient amount of input-output data pairs are available.

The alternative aspect provides a machine learning framework that can learn computationally expensive adaptive beamforming algorithms from a limited amount of training datasets and apply the learned algorithms on new datasets at a significantly lower computational cost via inference. The alternative aspect of the invention may be an enabler of real-time processing of computationally expensive adaptive beamforming algorithms that are otherwise very difficult to run in real-time, sometimes even with GPUs at an above-average price point.

The main element of the alternative aspect of the invention is a neural network that maps time-aligned complex per-channel RF data to complex beamformed RF data. While several types of neural networks like multi-layer perceptron (MLP), convolutional neural networks (CNN), and more advanced networks such as regressive and/or generative networks may be used to perform similar tasks, the alternative aspect uses MLP model to demonstrate the feasibility of using machine learning/deep learning framework to learn and apply an advanced adaptive beamforming technique. The MV beamformer is used as a test algorithm, but the core concepts presented here can be extended to other adaptive beamforming algorithms as well.

The input-output pairs used in training the neural network in the alternative aspect of the invention are not pixels from original and MV beamformer images, but rather the input data consists of time-aligned complex channel RF signals at a given depth and the output data is the corresponding complex beamformer output for the MV beamformer. The main steps are illustrated in FIG. 8. In step 1, the training data set for neural network training is prepared. It consists of the time-aligned complex per-channel data as input, and the complex MV beamformed RF data as target. For an N-channel system, M input-output pairs are obtained from 2N input per-channel data (real and imaginary) at a given pixel location and the corresponding MV beamformer output (real and imaginary). Both input and output data have real and imaginary parts. Hence, the input data matrix is M×2N and the output data matrix is M×2. The MV beamforming should be performed offline to obtain such input-output pairs. Because the MV beamforming is performed only once at the data preparation stage, the computational burden associated with it is not a limitation of the method.

In step 2, the training data set is used to train the learning algorithm. This step is performed iteratively until the mapping error converges to a certain pre-specified level. An MLP model was used to prove the concept. However, more advanced network architectures involving convolutional neural networks may be used. This will be described in more detail as an embodiment later.

In step 3, a test data set in the form of time-aligned complex per-channel data, which the learning algorithm has not observed before, is introduced. The trained algorithm operates on the input data to predict (or infer) its complex MV beamformer output. The inference step is expected to be significantly faster than direct computation of MVBF as it approximates computationally-intensive operations in MVBF using only additions and multiplications. For example, the computational complexity associated with standard DAS is linear with the number of elements, $O(N)$. However, the computational complexity for MVBF is proportional to the subarray size L and becomes $O(L^3)$ due to matrix inversions needed to compute the optimal aperture weights. However, using MLPs, the added computational burden can be significantly reduced, potentially making it more feasible for real-time processing.

Some preliminary simulation results are provided in FIGS. 9 and 10: FIG. 9 shows a training data set from simulated phantom containing a single large anechoic cyst, showing the original image (left), the neural network image (middle), and the true MVBF image (right). A 64-element P4-2 phased-array was simulated. All images are pre-scanconverted images and all images are displayed on a 60 dB dynamic range. Notice the MVBF image exhibits finer speckle size and reduced amount of sidelobes inside the cyst. The neural network image also shows reduced sidelobes in the cyst and slighter smaller speckle size.

FIG. 10 shows a test data set from simulated phantom containing 3 small anechoic cysts. The original image (left), the neural network image (middle), and the true MVBF image (right) are shown. A 64-element P4-2 phased-array was simulated. All images are pre-scanconvert images and all images are displayed on a 60 dB dynamic range. Notice the MVBF image exhibits finer speckle size and reduced sidelobes in the anechoic cyst. The neural network image also shows similar improvements.

Other network architectures could be used to learn the adaptive beamforming algorithm. The key component is that the network maps from per-channel inputs to beamformed outputs. For instance, a convolutional neural network is expected to give good results. The input data is the aligned, real (or complex) per channel data. Processing can be local (learning one pixel value from the relevant per channel data) or global (learning the whole beamformed RF frame from the whole aligned data stack). Local processing seems appropriate to imitate algorithms (such as the minimum variance beamformer) whose input data is local anyways. Global algorithms also have to potential to learn and use anatomy information, provided enough data is provided.

In keeping with the philosophy of this alternative aspect of the invention, the following describes a local approach with convolutional neural network. The aligned per-channel data for each pixel is cropped in fast time around the sample depth of interest, yielding a (numTime*numElements) data matrix. The time dimension is typically a few wavelengths to be sensitive to steering effects. The training dataset size is determined by the number of such data windows in the number of available images. One single image can typically yield hundreds of thousands of independent training input-output pairs. A fully convolutional neural network with receptive field spanning the full input data and outputting a single scalar can be trained to learn the adaptively beamformed value at the depth of interest.

The above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

The invention claimed is:

1. A method for adaptive beamforming of ultrasound signals, the method comprising the steps of:
   a) receiving RF signals acquired by multiple ultrasound transducer elements in response to an ultrasound transmission;
   b) performing time-of-flight correction on the received RF signals to generate time-aligned RF signals;
   c) determining content-adaptive apodization weights for beamforming the RF signals by applying a trained artificial neural network to the time-aligned RF signals, wherein the trained artificial neural network takes the time-aligned RF signals as input and outputs the content-adaptive apodization weights; and d) applying the content-adaptive apodization weights to the time-aligned RF signals to calculate a beamformed output signal that corresponds to a single pixel in an ultrasound image within a field-of-view of the ultrasound transmission.

2. The method of claim 1, wherein the number of input nodes and the number of output nodes of the trained artificial neural network corresponds to the number of contributing time-aligned RF signals.

3. The method of claim 1, wherein the trained artificial neural network comprises at least one activation layer, including an activation function, which propagates both positive and negative input values with unbounded output values.

4. The method of claim 1, wherein the neural network comprises at least one activation layer, including an activation function which concatenates the positive and the negative part of input values.

5. The method of claim 1, wherein the artificial neural network comprises at most four fully connected layers.

6. The method of claim 1, wherein the artificial neural network comprises at most three activation layers.

7. The method of claim 1, wherein the beamformed output signal is used to reconstruct an ultrasound image of a field-of-view, and wherein the received RF signals are rearranged prior to applying the trained artificial neural network, so that the RF data relating to one or at most a few pixels of the ultrasound image are processed in one or more batches by the artificial neural network.

8. The method of claim 1, wherein the artificial neural network comprises at least one convolutional layer, in addition to or as an alternative to one or several fully-connected layer(s).

9. The method of claim 1, wherein the artificial neural network is part of a recurrent neural network.

10. The method of claim 1, wherein some or all of the weights of the artificial neural network are quantized, in particular quantized to 1 to 4 bits.

11. The method claim 1, wherein the artificial neural network comprises at least one hidden layer having fewer nodes than the input layer and/or the output layer of the artificial neural network.

12. The method of claim 1, wherein steps a)-d) are repeated for a plurality of batches of RF signals, wherein each batch of RF signals corresponds to the RF signals contributing to a different pixel in the ultrasound image within the field-of-view of the ultrasound transmission.

13. A method for providing a trained artificial neural network useful in content-adaptive beamforming of ultrasound signals, the method comprising:
a) receiving input training data including time-aligned RF signals acquired by multiple ultrasound transducer elements in response to an ultrasound transmission,
b) receiving output training data, wherein the output training data are content-adaptive apodization weights, wherein such content-adaptive apodization weights have been calculated from the time-aligned RF signals by a content-adaptive beamforming algorithm, in particular a minimum variance algorithm; or wherein the output training data are beamformed output signals calculated from the time-aligned RF signals by a content-adaptive beamforming algorithm;
c) training an artificial neural network by using the input training data and the output training data; and
d) providing the trained artificial neural network, wherein the trained artificial neural network takes the time-aligned RF signals acquired by multiple ultrasound transducer elements as input and outputs content-adaptive apodization weights for beamforming an output signal that corresponds to a single pixel within a field-of-view of a corresponding ultrasound transmission.

14. A computer program comprising instruction, which, when the program is executed by a computational unit, causes the computational unit to carry out the method of claim 13.

15. A system for adaptive beamforming of ultrasound signals, the system comprising:
a) first interface, configured for receiving RF signals acquired by multiple ultrasound transducer elements in response to an ultrasound transmission;
b) a computational unit, configured for:
performing a time-of-flight correction on the received RF signals to generate time-aligned RF signals;
applying a trained artificial neural network to the time-aligned RF signals, whereby the trained artificial neural network takes the time-aligned RF signals as input and outputs the content-adaptive apodization weights for beamforming the time-aligned RF signals arc generated, and for
applying the content-adaptive apodization weights to the time-aligned RF signals to calculate a beamformed output signal; and
c) a second interface, configured for outputting the beamformed output signal.

16. The system of claim 15, wherein the received RF signals include only a sub-set of RF signals acquired by a corresponding sub-set of the multiple ultrasound transducer elements.

17. The system of claim 15, wherein the number of input nodes and the number of output nodes of the trained artificial neural network corresponds to the number of contributing time-aligned RF signals.

18. The system of claim 15, wherein the trained artificial neural network comprises at least one activation layer, including an activation function, which propagates both positive and negative input values with unbounded output values.

19. The system of claim 15, wherein the artificial neural network comprises at most four fully connected layers.

20. The system of claim 15, wherein some or all of the weights of the artificial neural network are quantized, in particular quantized to 1 to 4 bits.

* * * * *